United States Patent [19]

Alexander et al.

[11] 4,425,337

[45] Jan. 10, 1984

[54] ADJUVANTS FOR RECTAL DELIVERY OF DRUG

[75] Inventors: Jose Alexander; Joseph A. Fix, both of Lawrence, Kans.

[73] Assignee: Merck & Co., Inc., Rahway, N.J.

[21] Appl. No.: 335,498

[22] Filed: Dec. 30, 1981

[51] Int. Cl.³ ...................... A61U 31/54; A61U 31/71
[52] U.S. Cl. .................................... 424/181; 424/247
[58] Field of Search ................................ 424/181, 247

[56] References Cited

U.S. PATENT DOCUMENTS 3,689,646 9/1972 Sevag .................................. 424/181

Primary Examiner—Stanley J. Friedman

Attorney, Agent, or Firm—M. A. Monaco; M. C. Sudol, Jr.

[57] ABSTRACT

A method and drug form enhancing the rate of absorption of a rectally administered drug from the rectal compartment into the blood stream of a warm blooded animal. The method includes the steps of preparing a drug form capable of being rectally administered. The drug form comprises a therapeutically effective unit dosage amount of a selected drug of the type which is capable of being absorbed into the blood stream from the rectal compartment and phenothiazines or salts thereof being present in the drug form in a sufficient amount to be effective in enhancing the drug absorption rate, when rectally administering the drug form to warm blooded animals.

4 Claims, No Drawings

ADJUVANTS FOR RECTAL DELIVERY OF DRUG

BACKGROUND OF THE INVENTION

Field of the Invention and Description of the Prior Art

This invention relates to a method for administering drugs to warm blooded animals by rectal delivery and it particularly relates to a method for enhancing the rate of absorption of such rectally delivered drugs from the rectal compartment to the blood stream; this invention also relates to improved rectal suppository drug forms used in the practice of such method.

One known method of drug administration is accomplished by the incorporation of a drug in a "suppository", which generally speaking, is a medicated solid dosage form generally intended for use in the rectum, vagina, and to a lesser extent, in the urethra. Molded rectal suppositories usually employ vehicles that melt or soften at body temperatures so that the drug may be released for use. On the other hand, soft elastic gelatin capsule suppositories rely on the presence of moisture in the rectum which causes the capsule to open and release its contents which contains its therapeutic agent. Drugs administered in suppository form are administered for either local or systemic effect. The action of the drug is dependent on the nature of the drug, its concentration, and its rate of absorption. Although rectal suppositories are commonly used for the treatment of constipation and hemorrhoids, that is, for local effect, such rectal suppositories are also administered rectally for systemic action. A wide variety of drugs may be rectally administered, as by the use of suppositories, including, for example, analgesics, antispasmodics, sedatives, tranquilizers, and antibacterial agents.

Rectal drug administration has many advantages over other routes of drug administration, such as oral administration and parenteral administration. For example, many drug substances that are given orally undergo inactivation in the stomach because of the acidic, enzymatic content of the stomach or the drug may be subject to digestive attack in the gut and/or to microbial degradation in the lower gut. Oral administration of drugs also directs all of the absorbed substances through the liver where they can be inactivated or reduced in effectiveness.

Rectal administration overcomes wholly, or in part, these known disadvantages of oral drug administration. Rectal drug administration also has advantages over parenteral administration. For example, rectal drug administration does not require highly trained personnel required for parenteral administration and also represents significantly less hazard to the patient.

In view of the known disadvantages of oral and parenteral drug administration, drug administration by rectal delivery enables many drugs to be absorbed from the anorectal area, and yet retain their therapeutic value. The lower hemorrhoidal vein, surrounding the colon and rectum, enters the inferior vena cava and thereby bypasses the liver. Therefore, drugs are absorbed directly into the general circulation when rectally administered. For further background on rectal delivery of drugs, reference is made herein to an article entitled "Rectal Administration of Drugs" by N. Senior, "Advances in Pharmaceutical Sciences", edited by Bean, Beckett, and Corlass, Volume IV, Academic Press (1974) and to Chapter 8, "Suppositories", by Joachim Anschel and Herbert A. Lieberman, Lachman and Lieberman "Theory and Practice of Industrial Pharmacy", Lea and Febiger (1976).

Despite the known advantages of rectal administration of drugs, the rectal administration of drugs is not totally without problems. First, many rectally administered drugs are poorly absorbed while others are slowly absorbed and, if so, are often inactivated or degraded while still in the rectal compartment. It would therefore be highly advantageous if rectally administered drug substances could have their rate of absorption from the rectal compartment to the blood stream enhanced.

SUMMARY OF THE INVENTION

It is therefore an important object of the present invention to provide a unique method for enhancing the absorption rate of rectally administered drugs from the rectal compartment to the blood stream.

It is also an object of the present invention to provide an improved rectal suppository drug form which enhances the absorption rate of rectally delivered drugs contained in a soft elastic gelatin capsule or a molded suppository.

It is a further important object of the present invention to provide an improved method for administering drugs by the use of rectal suppositories wherein enhanced absorption results from the incorporation of phenothiazine or salts thereof into the drug formulation.

It is yet another important object of this invention to provide an improved rectal suppository having an enhanced absorption rate of a selected drug therefrom when in the rectal compartment, wherein phenothiazines or salts thereof are incorporated into a drug formulation contained within a soft elastic gelatin capsule or molded type of rectal suppository.

Further purposes and objects of this invention will appear as the specification proceeds.

The foregoing objects are accomplished by providing a method and suppository drug form wherein the absorption rate of rectally administered drugs into the bloodstream of warm blooded animals is enhanced, the method comprising the steps of preparing a drug form capable of being rectally administered, the drug form comprising an effective unit dosage amount of a drug of a type which is capable of being absorbed from the rectal compartment into the blood stream, and phenothiazines or salts thereof, the phenothiazines or salts thereof being present in said drug form in an amount sufficient to be effective in enhancing the absorption rate of a drug into the blood stream from the rectal compartment, and thereafter rectally administering the drug form to a warm blooded animal.

DETAILED DESCRIPTION OF THE PREFERRED EMBODIMENTS

The present invention, generally, comprises the steps of preparing a drug form capable of being rectally administered, wherein the drug form comprises an effective unit dosage amount of a drug capable of being absorbed into the blood stream of a warm blooded animal from the rectal compartment and phenothiazines or salts thereof being present in the drug form in a sufficient amount to be effective in enhancing the absorption rate, and rectally administering the drug form to the warm blooded animal.

Our method for enhancing the rate of absorption of drugs from the rectal compartment is useful for a wide range of drugs or drug categories including, but not limited to $\beta$-lactam antibiotics such as penicillin, including penicillin G., penicillin V., ampicillin, amoxicillin, methacillin, carbenicillin, ticaricillin and cephalosporins, such as cephalosporin C, cefazolin, cefoxitin, cephamandole, cefuroxine, cephapirin, cephaloridine, cephmetazole, cephanone and oxacephalosporin, all of which drugs are capable of being absorbed into the blood stream of a patient from the rectal compartment. Other drug catagories include xanthines, anticancer agents, other antibiotics (such as erythromycin, thienamycin and derivatives thereof such as N-formimidoyl thienamycin and gentamicin), antiarrythmics, polypeptides, cardiovascular agents, antidiabetics, antiulcers, antifungals, antinauseants, sedatives, diuretics, antihypertensives, anti-inflammatories, anticoagulents, antihelminthics, antiviral agents, radioopaques and radionuclide diagnostic agents, polynucleotides and drugs for the treatment of Parkinsons disease. Still other specific drugs useful in the method and in combination with the hereinafter described adjuvants are hereinafter identified, particularly in Example 2. The amount of the drug used in our method for enhancing drug absorption varies over a wide range, generally any therapeutically effective unit dosage amount of the selected drug is used.

The compounds that are used as adjuvants in our method and in our suppositories are known generally as phenothiazines and have the following formula I:

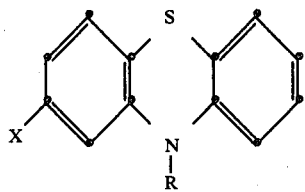

wherein X is hydrogen, alkyl, alkenyl, halo (F, Cl, Br or I), trihaloalkyl, hydroxyalkyl, alkoxy, ketoalkyl, thioalkyl, alkyl sulfoxide, mono- or dialkyl sulfonamide, alkyl sulfone, or cyano and R is dialkylaminoalkyl, N-alkylpiperazino alkyl or N-alkylpiperidinoalkyl and N-alkylpiperazinoalkyl or N-alkylpiperidinoalkyl wherein the piperidino and piperazino ring may be substituted by halo, haloalkyl, hydroxyalkyl, alkoxy, keto alkyl, thioalkyl, alkylsulfoxide, mono- or dialkyl sulfanomide, alkylsulfone, cyano, hydroxy, carbamido, dialkylamido, carbalkoxy alkyl, carboxy, carbalkoxy, amino, or mono- or dialkylamino and the pharmaceutically acceptable acid addition salts thereof.

Alkyl, wherever it appears, means straight or branched chain groups having up to 4 carbon atoms, such as for example methyl, ethyl, propyl, isopropyl, butyl, isobutyl and the like. Alkenyl means a group having from 2 to 4 carbon atoms such as allyl and the like.

Preferred phenothiazines are those of formula I and the pharmaceutically acceptable acid addition salts thereof wherein:

R is dialkylamino alkyl such as N,N-dimethylaminopropyl, N-alkyl piperazino alkyl such as N-methylpiperazino propyl, N-alkylpiperadinoalkyl such as N-methylpiperadino ethyl or N-alkyl piperazino alkyl wherein the piperazino group is substituted with hydroxyalkyl such as hydroxy ethyl;

and X is hydrogen, alkyl, halo (particularly chloro), trihalo alkyl particularly trifluoromethyl, thioalkyl, alkylsulfoxide such as sulfoxomethyl and keto alkyl such as ketomethyl.

Typical phenothiazenes which can be combined with the drugs mentioned in this invention are:
promazine
propiomazine,
chlorpromazine,
perphenazine,
fluphenazine,
acetophenazine,
butaperazine,
prochloroperazine,
carphenazine,
thiopropazate,
trifluorperazine,
thioridazine,
mesoridazine, and
piperacetazine,
and the pharmaceutically acceptable acid addition salts of any of these phenothiazines.

The term "pharmaceutically acceptable acid addition salt" as used herein generally includes the nontoxic acid addition salts of the phenothiazine compounds of formula (I), formed with nontoxic inorganic or organic acids. For example, the salts include those derived from inorganic acids such as hydrochloric, hydrobromic and the like; and the salts prepared from organic acids such as acetic, stearic, tartaric, maleic and the like. These salts and their preparation from the parent phenothiazine are well known by those skilled in this art.

As in the case of the drugs used in our method and suppositories, the amount of adjuvant used may vary over a wide range; in general, the identity and the amount of the adjuvant used in connection with the drug are selected in order to be effective in enhancing the absorption rate of the drug from the rectal compartment into the bloodstream.

Generally the amount of adjuvant in our drug forms (suppositories) is from 10–500 mg in each unit dose. The percentage of adjuvant in the total combination of drug plus adjuvant is 5–50% with a preferred ratio of adjuvant in the total combination of adjuvant plus drug being 5–30%.

The particular method used for the rectal administration of the drug and the adjuvant is preferably by use of the appropriate size, shape or form of any of the various types of rectal suppositories known to the pharmaceutical art; alternatively, the drug may be administered with the adjuvant by means of microenema. Useful rectal suppositories with which the present method may be used include cocoa butter suppositories, synthetic fat suppositories, and gelatin capsules including soft elastic gelatin capsule type suppositories as well as other controlled release devices such as an osmotic pump or other polymeric devices.

A preferred form of suppository comprises a soft elastic gelatin capsule having an outer shell which encloses the drug and the adjuvant in a suitable vehicle which will not attack the walls of the seamless gelatin capsule. The shell encapsulates a preselected drug form and the adjuvant. The gelatin capsule shell may be formulated in accordance with conventional techniques for making filled, seamless, soft elastic gelatin capsules containing therapeutically effective unit dosage amounts of the active drug ingredient. For example one conventional shell formulation includes about 30–53 parts by weight of gelatin, 15–48 parts by weight of a plasticizer, such as glycerine or sorbitol, and about 16-40 parts by weight of water. Additionally, the gelatin shell may contain preservatives such as mixed parabens, ordinarily methyl or propyl parabens in a about a 4-1 ratio. The parabens may be incorporated in the shell formulation in minor proportions as compared to the total weight of the shell formulation. Conventional gelatin capsules utilize gelatin having a bloom value of about 160-200 although this amount may be varied.

In a conventional manner, the gelatin composition is mixed and melted under vacuum conditions. The capsules may be simultaneously formed and filled using a conventional method and apparatus. The gelatin capsules are formed into a desired shape and size for insertion into the rectal compartment. It is to be understood, however, that the particular method used for making the soft elastic gelatin shell and for incorporating the fill therein are not considered part of the invention herein.

One of the more important uses of our method and suppository for rectal administration of drugs is in the administration of sustained release or programmed release drug forms which will slowly release the drug substances into the rectal compartment of a warm blooded animal. The present method and suppository permit the rapid clearance of the released drug into the blood stream by way of the lower hemorrhoidal vein, instead of moving upwards into the lower gut. This technique thereby reduces or avoids loss of drug effectiveness associated with passage of the drug through the liver.

The following data sets forth specific experiments illustrating various embodiments of the present invention.

EXAMPLE 1

Method: Adult male Sprague/Dawley rats (anesthetized with ethylcarbamate) were given intra-rectal aqueous microenemas. Microenemas are defined as small volume (0.3 ml) aqueous solutions containing drug/adjuvant compounds, administered with a 1 cc syringe at an intra-rectal depth of 2.5 cm. Bioavailabilities versus intravenous administration were calculated as a measure of drug delivery according to the following formula:

$$\% \text{ Bioavailability} = \frac{(AUC)_{rectal} \times (Dose)_{i.v.} \times 100}{(AUC)_{i.v.} \times (Dose)_{rectal}}$$

wherein

AUC means area under serum drug level curve from $t=0$ minutes to $t=90$ minutes.

Dose is in mg.

Data from screening the adjuvant for rectal absorption promoting potential with gentamicin sulfate and sodium cefoxitin follow.

| | % Bioavailability ± SEM | | | |
|---|---|---|---|---|
| | Gentamicin | Drug n | Cefoxitin | n |
| None | 1 ± 0.7 | 4 | 2 ± 0.6 | 3 |
| Chlorpromazine | 107 ± 6.2 | 3 | — | — |
| Perphenazine | 100 ± 8.3 | 3 | 62 ± 4.7 | 3 |
| Tiorioazine | 115 ± 11.5 | 3 | 38 ± 3.5 | 3 |
| Triflupromazine | 146 ± 14.9 | 3 | 58 ± 8.0 | 3 |
| Fluphenazine | 143 ± 4.6 | 3 | 49 ± 5.0 | 3 |
| Promazine | 76 ± 3.5 | 3 | 41 ± 6.8 | 3 |
| Trifluoperazine | 74 ± 6.6 | 3 | 68 ± 0.6 | 3 |
| Prochlorperazine | 76 ± 10.9 | 3 | 16 ± 3.7 | 3 |

The cefoxitin or gentamicin was administered as sodium cefoxitin or gentamicin sulfate at 10 mg/kg body weight. The adjuvants were administered at 20 mg/kg body weight and n represents the number of animals.

Gentamicin bioavailability: Concentration curves for chlorpromazine and perphenazine in rat microenema rectal delivery system.

| Adjuvant | Dose (mg/kg body weight) | % Bioavailability ± SEM |
|---|---|---|
| Perphenazine | 1 | 16 ± 10.7 |
| | 2.5 | 31 ± 8.0 |
| | 5 | 49 ± 6.8 |
| | 10 | 86 ± 20.7 |
| | 20 | 100 ± 8.3 |
| Chlorpromazine | 1 | 30 ± 5.8 |
| | 2.5 | 44 ± 5.7 |
| | 5 | 60 ± 2.5 |
| | 10 | 103 ± 1.8 |
| | 20 | 107 ± 6.2 | n = 3 animals for each concentration.
Control bioavailability (without adjuvant) = 1 ± 0.7% (n = 3).
Gentamicin administered at 10 mg kg body weight.

EXAMPLE 2

Following the procedure of Example 1 but using an appropriate amount of the following drugs in place of gentamicin or cefoxitin used in Example 1 the corresponding drug/adjuvant mixture is produced. β-lactam antibiotics.

Following is a representative table of drugs, which in combination with the appropriate adjuvant, are evaluated in accordance with the method described above:

β-Lactam Antibiotics

1. Ampicillin
2. Amoxicillin
3. Methacillin
4. Cephapirin
5. Cefalothin
6. (6R-cis)-3-[[(Aminocarbonyl oxy]methyl]-7-methoxy-8-oxo-7-[(2-thienylacetyl)) amino]-5-thia-1-azabicyclo [4.2.0]oct-2-ene-2-carboxylic acid (cefoxitin);
7. Carbenicillin
8. Penicillin G
9. Ticaricillin
10. Cefazolin
11. Cephaloglycin
12. Cephaloridine
13. Cephalosporin C
14. Cephmetazole
15. Oxacephalosporin
16. Penicillin V
17. N-formimidoyl thienamycin monohydrate
18. Cephalexin
19. Carbenicillin
20. Cephmandole.

Other antibiotics

Erythromycin
Thienamycin and derivatives thereof
N-formimidoyl thienamycin
(6R-cis)-3-[[Aminocarbonyloxy]methyl]-7-methyoxy-8-oxo-7-[(2-thienylacetyl))amino]-5-thia-1-azabicyclo-[4.2.0]oct-2-ene-2-carboxylic acid (cefoxitin)

1-ethyl-6-fluoro-1,4-dihydro-4-oxo-7-(1-piperazinyl)-3-quinolinecarboxylic acid
3-fluoro-D-alanine and D-4-(1-methyl-3-oxo-1-butenylamino)-3-isoxazolidinone sodium salt hemihydrate
7-[(hydroxyphenylacetyl)amino]-3-[[(1-methyl-1H-tetrazol-5-yl)thio]methyol]-8-oxo-5-thia-1-azabicyclo-[4.2.0]oct-2-ene-2-carboxylic acid (cephamandole)
1-ethyl-1,4-dihydro-7-methyl-4-oxo-1,8-naphthyridine-3-carboxylic acid (nalidixic acid)
6-[[amino(4-hydroxyphenyl)acetyl]-amino]-3,3-dimethyl-7-oxo-4-thia-1-azabicyclo-[3.2.0]heptane-2-carboxylic acid (amoxicillin)
gentamycin.

Xanthines 3,7-Dihydro-1,3-dimethyl-1H-purine-2,6-dione (theophylline).

Anticancer agents

Allopurinol
Viscristine
Vinblastine
Methotrexate
Dactinomycin.

Antiarrhythmics 2-(Diethylamino)-N-(2,6-dimethyl-phenyl)acetamide (lidocaine)
Procainamide
Quinidine sulfate.

Polypeptides

| Insulin | Oxytocin | FSH |
|---|---|---|
| Stomatostatin and analogues | Endorphin | Substance P. |
| Calcitonin | Enkephalin | |
| Pentagastrin | Growth Hormone | |
| Gastrin | Prolactin | |

Cardiovascular agents

Antidiabetics

Insulin
Chloropropamide
Tolazamide.

Antiulcers

Cimetidine.

Antifungals

Griseofulvin
Amphotericin B
Miconazole

Antinauseants
Sedatives 3-(5H-dibenzo[a,d]cyclohepten-5-ylidene)-N,N-dimethyl-1-propanamine (cyclobenzaprine)
α-[2-[4-[(4-chlorophenyl)phenylmethyl]-1-piperazinyl]ethoxyethanol (hydroxyzine)]
7-chloro-1,3-dihydro-1-methyl-5-phenyl-2H-1,4-benzodiazepin-2-one (diazepam)
7-chloro-N-methyl-5-phenyl-3H-1,4-benzodiazepin-2-2-amine 4-oxide (chlorodiazepoxide)
4-[4(4-chlorophenyl)-4-hydroxy-1-piperidinyl]-1-(4-fluorophenyl)-1-butanone (haloperidol)
Glutethimide

Diuretics 3,5-diamino-N-(aminoimino-methyl)-6-chloropyrazinecarboxamide (amiloride)
6-chloro-3,4 dihydro-2H-1,2,4-benzothiadiazine-7-sulfonamide-1,1-dioxide (hydrochlorothiazide)
amiloride hydrochloride and hydrochlorothiazide (moduretic).

Antihypertensives 3-hydroxy-α-methyl-L -tyrosine (methyldopa)
S-(−)-1-(tert-butylamino)-3-[(4-morpholino-1,2,5-thiadiazol-3-yl)oxy]-2-propanol (timolol)
N-[(S)-1-(ethoxycarbonyl)-3-phenylpropyl]-L-alanyl-L-proline maleate 2-(2,6-dichloroanilino)-2-imidazoline (clonidine)
5-(aminosulfonyl)-4-chloro-2-[(2-furanylmethyl)amino]benzoic acid (furosemide).

Drugs for the treatment of Parkinsons disease:

S-α-hydrozino-3,4-dihydroxy-α-methylbenzenepropanoic acid monohydrate (carbidopa)
carbidopa and 3-hydroxy-L-tyrosine (levodopa) (Sinemet)
3-hydroxy-L-tyrosine (levodopa), (L-Dopa)
Benzotropine mesylate.

Anti-inflammatory

2',4'-difluoro-4-hydroxy-[1,1'-biphenyl]-3-carboxylic acid (diflunisal)
1-(p-chlorobenzoyl)-5-methoxy-2-methylindole-3-acetic acid (indomethacin)
(Z)-5-fluoro-2-methyl-1-[[4-(methylsulfinyl)phenyl]methylene]-1H-indene-3-acetic acid (sulindac)
α-methyl-4-(2-methylpropyl)benzeneacetic acid (ibuprofen)
(+)-6-methoxy-α-methyl-2-naphthaleneacetic acid (Naproxen)
5-(4-chlorobenzoyl)-1,4-dimethyl-1H-pyrrole-2-acetic acid (Zomepirac)
4-butyl-1,2-diphenyl-3,5-pyrazolidinedione (phenylbutazone)
9-fluoro-11β,17,21-trihydroxy-16a-methylpregna-1,4-diene-3,20-dione (dexamethasone)
11β,17,21-trihydroxypregna-1,4-diene-3,20 -dione (prednisolone).

Anti-coagulant

Heparin

Antihelminthics

Ivermectin
Chloroquine.

Antiviral Agents

Ara A
Ara C
Acycloguanosine
Amantadine hydrochloride.

Radio-opaques and radio-nuclide diagnostic agents

Polynucleotides (−)-1-(cyclopropylmethyl)-4-[3-(trifluoromethylthio)-5H-dibenzo(a,d)cyclohepten-5-ylidene]piperidine hydrochloride (+)10,11-dihydro-5-methyl-5H-dibenzo[a,d]cyclohepten-5,10-imine oxalate L-N (2-oxopiperidin-6-yl-carbonyl)-histidyl-L-thiazolidine-4-carboxamide.

EXAMPLE 3

Following the procedure of Examples 1 and 2 but using appropriate amounts of the following adjuvants in place of the adjuvants used in Example 1, one can obtain the appropriate drug/adjuvant mixture.

| Chlorpromazine | Mesoridazine |
|---|---|
| Perphenazine | Piperacetazine |
| Thioridazine | Acetophenazine |
| Triflupromazine | Butoperazine |
| Fluphenazine | Carphenazine |
| Promazine | Methophenazine |
| Trifluoperazine | Propionazine |
| Prochlorperazine | Thiopropazate |

While in the foregoing there has been provided a detailed description of particular embodiments of the present invention, it is to be understood that all equivalents obvious to those having skill in the art are to be included within the scope of the invention as claimed.

What is claimed is:

1. A method for enhancing the rate of absorption of a rectally administered drug from a rectal compartment into the blood stream, said method comprising the steps of preparing a drug form capable of being rectally administered, said drug form comprising a therapeutically effective dosage amount of a β-lactam antibiotic capable of being absorbed into the blood stream from the rectal compartment, and a phenothiazine of the formula:

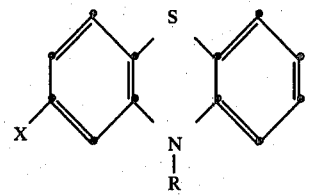

and the pharmaceutically acceptable acid addition salts thereof, wherein:

X is hydrogen, alkyl, halo, trihaloalkyl, thioalkyl, alkylsulfoxide or ketoalkyl; and R is dialkylaminoalkyl, N-alkylpiperazinoalkyl, N-alkylpiperazinoalkyl or N-alkylpiperidinoalkyl wherein additionally the piperazino group can be substituted with hydroxyalkyl thereof as adjuvant, said adjuvant being present in said drug form in a sufficient amount to be effective in enhancing said absorption rate and said adjuvant being present in the drug form at from 10–500 mg in each unit dose and being present in a ratio of 5% to 50% of adjuvant to adjuvant plus drug, and administering said drug form into said rectal compartment.

2. The method of claim 1 wherein said β-lactam antibiotic comprises cefoxitin, cefmetzole, cephamandole or amoxicillin.

3. The method of claim 1 wherein said drug comprises cefoxitin.

4. The method of claim 1 wherein said adjuvant comprises:

| chlorpromazine | mesoridazine |
|---|---|
| perphenazine | piperacetazine |
| thioridazine | acetophenazine |
| triflupromazine | butoperazine |
| fluphenazine | carphenazine |
| promazine | methophenazine |
| trifluoperazine | propionazine |
| prochlorperazine | thiopropazate | or a pharmaceutically acceptable acid addition salt thereof.

* * * * *